United States Patent [19]

Schenck

[11] Patent Number: 4,474,181

[45] Date of Patent: Oct. 2, 1984

[54] METHOD AND APPARATUS FOR ANASTOMOSING SMALL BLOOD VESSELS

[76] Inventor: Robert R. Schenck, 1100 N. Lake Shore Dr., Apartment 33A, Chicago, Ill. 60611

[21] Appl. No.: 349,885

[22] Filed: Feb. 18, 1982

[51] Int. Cl.³ .............................................. A61B 17/11
[52] U.S. Cl. .................................................. 128/334 R
[58] Field of Search ............... 128/334 R, 334 C, 335, 128/340, 326, 346

[56] References Cited

U.S. PATENT DOCUMENTS

| | | | |
|---|---|---|---|
| 3,155,095 | 11/1964 | Brown | 128/334 C |
| 3,180,337 | 4/1965 | Smialowski | 128/334 |
| 3,254,650 | 6/1966 | Collito | 128/334 |
| 3,254,651 | 6/1966 | Collito | 128/334 C |
| 4,055,186 | 10/1977 | Leveen | 128/334 C |
| 4,165,747 | 8/1979 | Bermant | 128/334 C |

FOREIGN PATENT DOCUMENTS 2101284 1/1970 Fed. Rep. of Germany ........ 292/70

OTHER PUBLICATIONS

Nakayama et al., *Surgery* Dec. 1962, pp. 918–931.
Berakha et al., *Surgical Forum* 26 (1975) pp. 550–555.

*Primary Examiner*—Michael H. Thaler
*Attorney, Agent, or Firm*—Fitch, Even, Tabin & Flannery

[57] ABSTRACT

A member, preferably in the form of a ring, is provided to simplify anastomosing severed ends of blood vessels and insuring patency of the anastomized blood vessels. The member has an interior surface significantly larger than the outside diameter of the blood vessel and means at least three spaced-apart locations for tethering blood vessel-connecting sutures thereto.

The ring is disposed around one of the severed ends of the blood vessel, the ends of the blood vessel are connected with at least three sutures at spaced apart locations and the sutures are tethered to the ring to apply outward radial stress to the connected blood vessels, which radial stress in several directions helps to assure patency of the anastomosed blood vessel.

21 Claims, 10 Drawing Figures

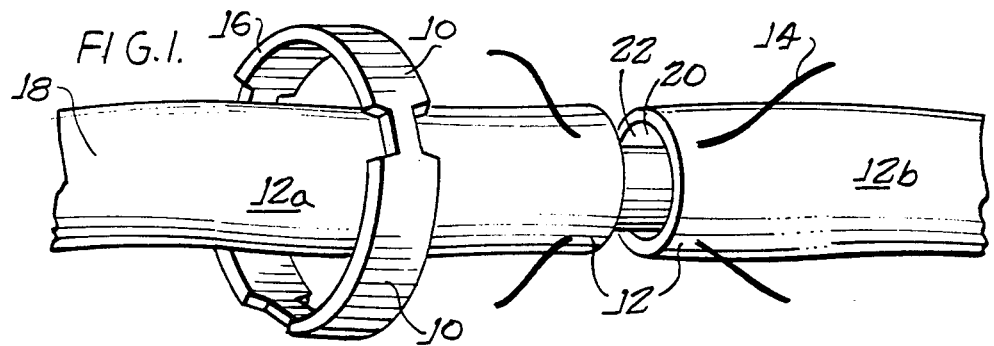
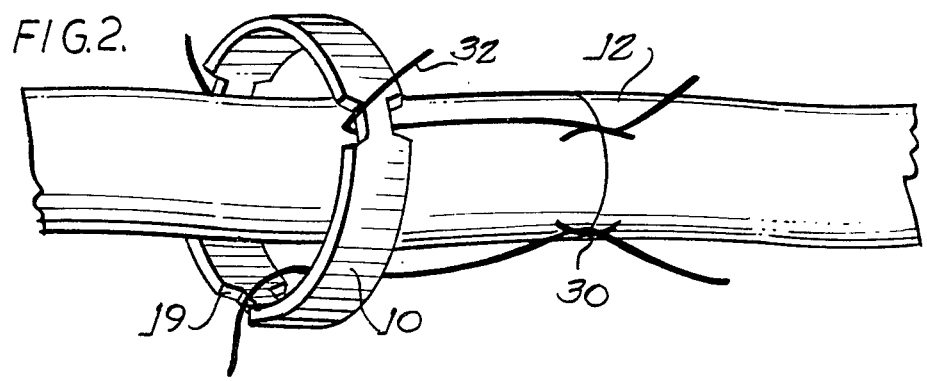
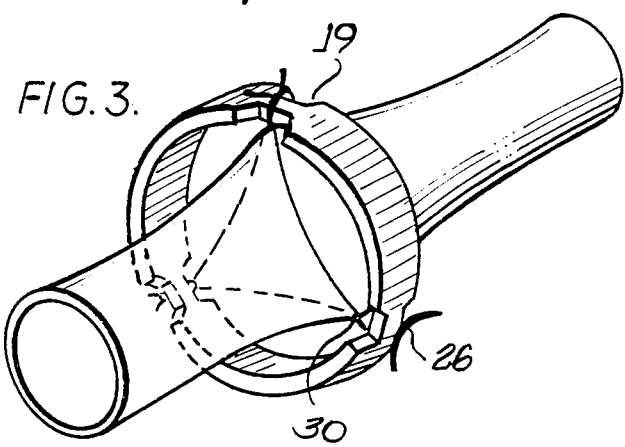
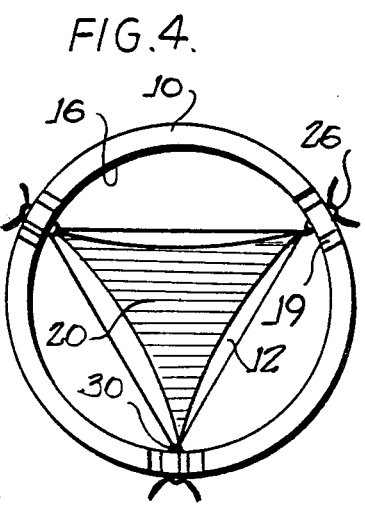
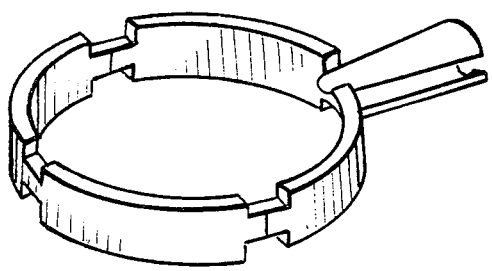

METHOD AND APPARATUS FOR ANASTOMOSING SMALL BLOOD VESSELS

The present invention relates to methods and apparatus for joining severed ends of blood vessels.

Among the important and time consuming tasks in surgical procedures is the anastomosis or joining of severed blood vessels, and the success of a surgical procedure may depend on the degree of circulation which is restored through such anastomosis. Anastomosing of blood vessels is a tedious procedure, particularly in blood vessels of small diameter including blood vessels less than 11 mm. in diameter. Conventional suturing techniques are time consuming, extending the duration of an operation and their successful anastomosing is highly dependent on the proper placement of sutures by the surgeon. Particular difficulty is often encountered in anastomosing children's vessels which are small and prone to spasm.

To aid in anastomosing blood vessels, implantable devices which connect severed ends of the blood vessel have been described previously, e.g., U.S. Pat. Nos. 3,254,650 and 4,055,186, British Patent Specification No. 1,181,563, German Fed. Rep. Pat. No. 2,101,282 and Nakayama et al. *Surgery* December 1962, pp. 918-931. Devices have also been described for everting severed ends of blood vessels to facilitate suturing thereof, e.g., U.S. Pat. No. 2,180,337. The need continues for improved methods and apparatus for anastomosing blood vessels, particularly tiny blood vessels.

Blood vessels of all but the largest size, i.e., the aorta and vena cava in humans, have a naturally occuring contractility, identified as circumferential compressive stress, that resists dilation. These forces become proportionately larger as the vessel diameter decreases and the relative wall thickness increases. Radial tethering forces of tissues do exist around the vessel, but these are of lesser significance than longitudinal vessel motion tethering.

Successful suturing of blood vessels does not assure their continued patency, i.e., their ability to conduct blood flow. Thrombosis (clotting of blood) may act to block blood flow through an anastomosed vessel. In addition to inaccurate placement of sutures, several other factors—spasm, stensosis, and microclamp damage—may be additive in causing thrombosis after microvascular repair. It has been found that continuity of flow during the first twenty minutes after anastomosis to be critical in preventing thrombus formation. It has also been found that platelet aggregation, and later resolution occurs in the first several hours after a microvascular anastomosis.

It is a general object of the present invention to provide methods and apparatus which simplify surgical anastomosis techniques and which effect an anastomosis with substantial assurance of patency.

Herein, an external ring is provided which is placed around one end of the blood vessel to be joined. Three or more sutures are used to join the ends of the blood vessel, and the sutures are tethered to the ring at various circumferal locations to apply outward radial stress for maintaining an open blood flow passageway at the junction. The tethering holds the intima of the severed ends together forming a fluid-tight seal and promoting healing and minimizing both the number and exposure of the sutures, thereby reducing the likelihood of significant thrombosis occurring at the anostomosis site.

These and other objectives and advantages of the invention will become more apparent from the following detailed description of the invention in reference to the accompanying drawings in which:

FIG. 1 is a perspective view of an anastomosis ring, embodying various features of the invention, disposed around a severed end of blood vessel and sutures threaded through the blood vessel ends to be anostomosed;

FIG. 2 is a perspective view of an anastomosis ring of FIG. 1 showing the sutures tied to connect the blood vessel ends by sutures;

FIG. 3 is a perspective view of the ring of FIG. 1 with the sutures tethered to the ring;

FIG. 4 is a plan view showing one of the two severed ends sutured and tethered to the ring;

FIG. 6 is electron micrograph of a rat's blood vessel which has been severed and rejoined by the method and apparatus of the present invention;

FIG. 7 is a perspective view of an alternative embodiment of an anastomosis ring having means for tethering four blood vessel-connecting sutures;

FIG. 10 is a photo micrograph of an end-to-side rat blood vessel anastomosis.

Figure 5:
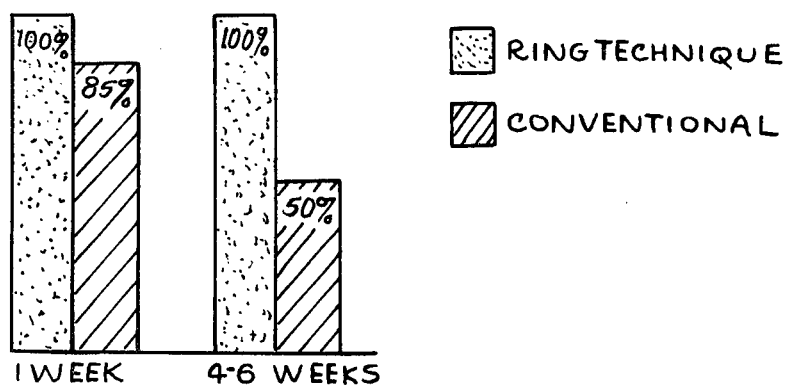
FIG. 5 is a bar graph representing patency of rat blood vessels sutured using the ring of the present invention as compared with suturing by conventional techniques.

In accordance with the present invention, severed blood vessel ends are reconnected with outward radial stress applied to the blood vessel at the anastomosis site to keep blood flow passageways dilated and otherwise maintain patency of the connected blood vessel ends by placing an external (to the blood vessel) member 10 around an end 12a of the severed blood vessel 12, suturing the ends 12a, b, with three or more sutures 14 and tethering the sutures to the external member which has an interior surface significantly larger than the outer surface 18 of the blood vessel. (It is to be understood that the blood vessel ends of the end-to-end anastomosis need not be ends of the same blood vessel).

The member 10, preferably in the form of an annular ring formed of material which is biocompatible for implantation in a living body of an animal, such as a human, has means 19, such as grooves or notches, at spaced-apart locations for tethering the sutures 14. The tethering of the connected blood vessel 12 not only holds the blood flow passageway 20 open but dilates the blood vessel enlarging the blood flow passageway thereby reducing the chance of thrombosis occurring and clogging the passageway. The stretching also serves to tightly appose the interior surfaces or intima 22 of the blood vessel to aid prompt healing.

The external anastomosis member 10 is shown in FIG. 1 is an annular ring, a shape which corresponds to the generally circular cross section of blood vessels 12. In order to provide for stretching of the connected blood vessel ends 12a, 12b toward the ring, the interior surface 16 of the ring has an inside diameter at least 25 percent longer than the outside diameter of the blood vessel which the ring is adapted to surround, and preferably the inside diameter of the ring is between 50 percent and 200 percent longer than the diameter of the blood vessel. Although there is no inherent upper limit on ring size as compared to the size of the blood vessel for anastomosis purposes, the ring, being a foreign object within the body, is preferably as small as possible consistant with suture attachment providing radial tethering stress. The ring need be no longer or no thicker than is consistant with its structural integrity.

External anastomosis rings 10 may be formed of any material of sufficient strength to support the tethered blood vessels and is biocompatible or can be made biocompatible with an appropriate coating. Suitable biocompatible materials include but are not limited to graphite, pyrolytic carbon, tungsten, tantalum and polymeric material, such as polytetrafluorethylene. In a preferred embodiment, the ring 10 is formed or a material, which is not only biocompatible but is dissolved or otherwise degraded after a period of time by the body of the animal. Suitable biocompatible materials for rings which are solubilized or otherwise degraded after a healing period include collagen and polyglycolic and/or polylactic acid.

The attachment means 19 provided at spaced-apart locations on the ring 10, facilitate tethering of the sutures 14 to the ring and maintain the positioning of suture ties 26 (FIG. 3) around the ring. At least three such attachment means 19 are provided in order to tether the connected blood vessel ends 12a, b at three locations and so insure an open passageway 20 in the connected, tethered blood vessel. The attachment means 19 are preferably evenly spaced, an arrangement which maximizes the passageway size for the number of sutures used, for example, if three attachment means are used, they are disposed about 120° apart around the ring. Increasing the number of attachment means 19, to which are tethered a corresponding number of sutures, tends to enlarge the passageway at the anastomosis site while permitting the use of a smaller tethering ring; however, each additional suture increases the time needed to join a blood vessel, and accordingly, it is generally preferred, particularly for smaller blood vessels, that only three attachment means 19 be provided for tethering three sutures 14. However, for larger blood vessels, a ring having up to six or more attachment means might be provided. In the illustrated embodiment, notches 19 in the ring 10 provide the means for attaching and positioning the sutures during tethering. Three pairs of notches 19 are illustrated, the notches of each pair being formed in opposite ends of the ring 10. While other means of attachment may be provided, notches 19 are simply formed and conveniently utilized during surgery, requiring no threading or other tedious and time consuming techniques. The surgeon need not tether the sutures 14 initially in the notches 19 but may shift loosely tethered sutures into the notches after the ties 26 have been initially knotted around unnotched portions of the ring 10.

To end-to-end anastomose a blood vessel 12, the ends of the blood vessel are prepared for suturing in a medically acceptable manner, and the ring 10 is placed around one of the severed ends 12a as seen in FIG. 1. The sutures 14, corresponding in number to the notches 19, are then threaded through the walls of the blood vessels at spaced apart locations (FIG. 1), each suture being threaded through both of the severed ends 12a, b in adjacent circumferal locations. The threaded sutures are then tied into a knot 30 (FIG. 2) connecting the severed ends 12a, b of the blood vessel and leaving a free end 32 of each suture with sufficient length for tethering to the surrounding ring 10. Thereafter, the free ends 32 of the sutures 14 are looped around the ring 10, drawn outward to pull the blood vessel ends radially outward toward the ring and tied into knots 26 located within the notches 19. The tethered sutures 14 stretch the blood vessel ends 12a, b providing a polygonal blood passageway, e.g., where three sutures are used, the passageway is generally triangular as best seen in FIG. 4. Because the walls of the blood vessel 12 are stretched, the blood vessel ends are dilated, and the polygonal opening provides a blood flow passageway 20 which is typically as large or larger than the natural circular passageway of the blood vessel.

The stretching of the blood vessels 12 by the tethering sutures 14 also helps to hold the intima 22 of the blood vessel ends 12a, 12b in tight apposition to each other, as seen in FIG. 4, so that a fluid-tight seal is formed therebetween and the blood primarily contacts the intima of the connected blood vessel ends. Fewer sutures 14 are used than are generally used in conventional anastomosis techniques, and the tenting effect achieved by tethering minimizes the exposure of the sutures 14 to flowing blood, thereby reducing suture-induced thrombosis.

Figure 8:
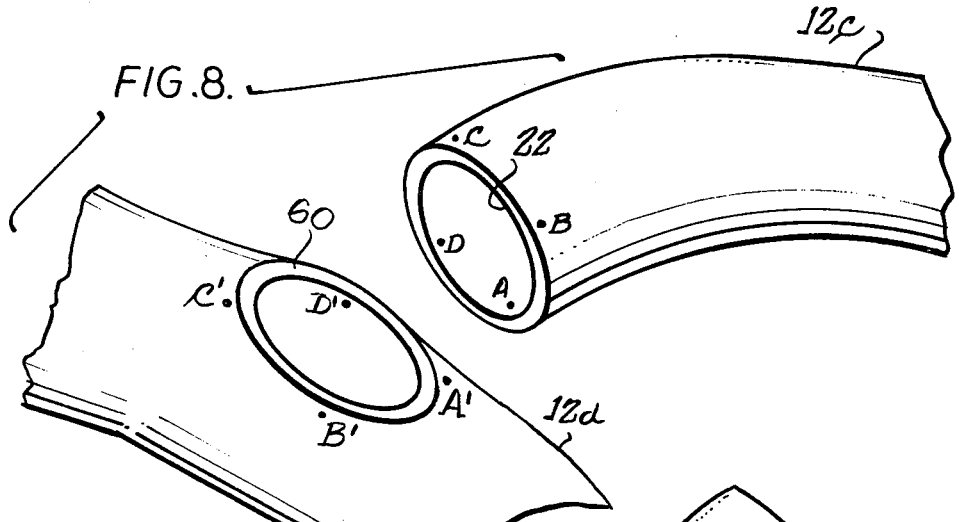
FIG. 8 is a perspective view of an end of one blood vessel prepared for anastomosis to a prepared side of another blood vessel.
Figure 9:
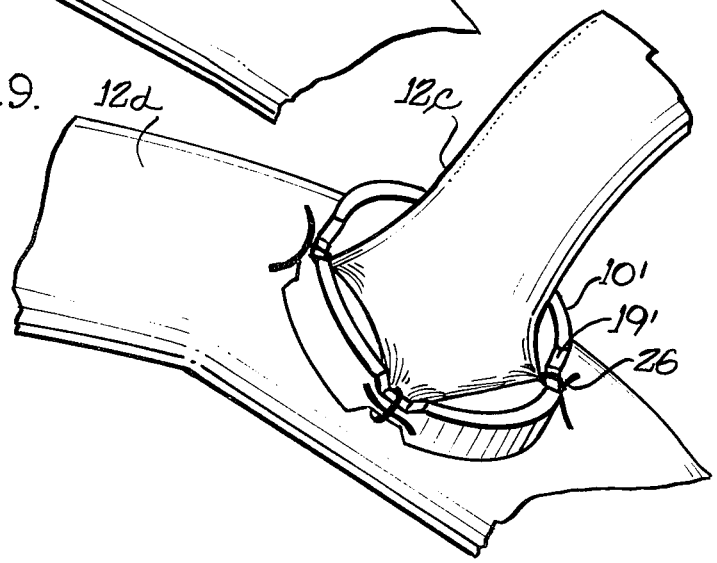
FIG. 9 is a perspective view of the end-to-side anastomosis performed with the ring of FIG. 7 on the prepared blood vessel of FIG. 8.

Illustrated in FIGS. 7-9 is an end-to-side anastomosis, such as may be used to form a shunt between one blood vessel and another. The illustrated anastomosis uses an anastomosis ring 10' having four notch pairs 19' spaced 90° from each other for attaching four tethering sutures 14. In this case, a prepared end portion 12c of one blood vessel is connected to another blood vessel portion 12d which has been prepared for anastomosis by cutting a generally circular opening 60, substantially the same size as the passageway 22, through side wall of the blood vessel end portion 12c. The interior diameter of the ring 10' is significantly larger than the exterior diameter of the blood vessel end portion 12c so that when the blood vessel portions 12c, d are joined, the ring is spaced radially outward from the anastomosis site, whereby the tethering sutures 14 apply outward stress to the connected portions.

Four discontinuous sutures are used to connect the prepared end portions 12c, d (FIG. 8) by threading them through locations, indicated at A, B, C, and D, generally evenly spaced around the circumference of the end portion 12c and corresponding locations A', B', C', and D', generally evenly spaced around the opening 60. The sutures 14 are tied to connect the portions 12c, d and then tethered to the four pairs of notches 19' to form the generally square anastomosis illustrated in FIG. 9.

The anastomosis members and their surgical uses will now be described in greater detail by way of specific example.

EXAMPLE I

Conventional and external ring technique anastomoses were performed on the superficial epigastric arteries on alternate sides of each of thirty male Sprague-Dawley strain rats weighing between 200 and 250 grams. Group 1 consisted of twenty external ring technique and twenty conventional technique anastomoses that were explored at one week, and again at four to six weeks. Group 2 consisted of ten external ring technique and ten conventional technique anastomoses that were left undisturbed until exploration at six weeks.

The rats were anesthetized with intraperitoneal pentobarbital, and the superficial epigastric artery was exposed through a transverse inguinal incision. External vessel diameters were 0.3 to 0.5 mm., measured prior to arterial isolation to avoid diameter variation induced by spasm or dilation due to smooth muscle relaxation by topical lidocaine. It was observed that an artery measuring 0.4 mm. in its undisturbed state could vary from 0.2 to 0.6 mm., from maximum vasoconstriction to maximum relaxation.

Three sutures 14 were used for the external ring technique, four to six sutures were used for the conventional anastomoses, dependent upon vessel diameter. Monofilament 100 nylon (Ethilon, Ethicon, tapir point BV75 needle) was used for all anastomoses and the operations were performed at 25x to 50x magnification. The pattern of arterial pulsation was observed, and a radical patency test was performed thirty minutes after completion of each anastomosis to confirm initial patency.

The anastomasis rings 10 comprised 1 mm lengths of 18 gauge polytetrafluorethylene tubing having pairs of trapezoidal notches 19 formed at three locations 120° apart. For the external ring technique, the blood vessel 12 was placed in an adjustable double microclamp and transected. The loose adventitia was resected and the vessel ends irrigated with heparinized saline solution. Prevention of spasm was aided by the external application of 1% lidocaine. The ring 10 was slipped over one vessel end 12a, and three interrupted sutures 14 were placed through the full thickness of the vessel wall at 120° intervals, leaving the suture ends 32 untied. The vessel ends 12a, b were approximated by tying a surgeon's knot 20, and a free end 32 of all three sutures 14 were passed underneath the ring (FIG. 3). The ring 10 was centered over the anastomotic site, and each of the sutures 14 were tied around the ring 10 at the location of the preformed notches 19 (FIG. 4). In cross section, the vessel 12 then assumed a triangular pattern at the anastomosis site, with the naturel elastic forces aiding tight apposition of the edges of the vessel intima between the three sutures 14. Distal release of the double microvascular clamp allowed retrograde flow, followed by proximal release and restoration of anterograde pulsatile flow.

In Group 1, all twenty external ring technique arterial anastomoses were patent both at one week and at four to six weeks. However, three of the twenty conventional anastomoses were thrombosed at one week, and an additional seven were thrombosed at four to six weeks (FIG. 5). Even among the originally patent, seventeen of the twenty conventional anastomoses, diminished flow during radical patency testing was abserved as compared to flow through anastomoses repaired with the external ring technique. This may have been a factor in the cases of later thrombosis. The difference between the 50% late patency rate by the conventional technique and the 100% patency rate by the external ring technique was statistically significant (p 0.001).

In Group 2, all ten external ring technique arterial anastomoses were patent at six weeks. In contrast, at six weeks, three of the ten conventional anastomoses were thrombosed and two others demonstrated diminished flow during radical patency testing. The difference between the 70% patency rate by the conventional technique and the 100% rate by the external ring technique again was statistically significant (p 0.02). In neither group was there any occurrence of aneurysms, hematomas or wound infections.

FIG. 6 is a scanning electron micrograph portraying one of the patent rat anastomosis performed by the external ring technique with normal intimal healing. It will be noted that slight tipping of the ring occurred; however, in no case did such tipping impede blood flow.

EXAMPLE II

Rat inferior epigastric veins (generally 0.7 mm. in diameter) were anastomosed end-to-side to femoral veins (generally 1.5 mm. in diameter) by conventional techniques in twenty control rats, using 6-8 sutures per anastomosis, and in an experimental group of twenty rats by the external ring technique using rings 1 mm. long of 18 gauge polytetrafluorethylene with four notch pairs spaced 90° apart. The surgical technique was substantially identical to that used in Example I, except that the femoral veins were prepared for anastomosis by cutting 6 mm. openings in their side walls.

After five days the control group has a 65% success rate whereas the experimental group exhibited 100% patency (p. 0.01).

FIG. 10 is a photo micrograph portraying one of the patent rat end-to-side anastomosis performed by the external ring technique with normal intimal healing.

The external ring technique provides a direct approach to overcome the vessel's inherent circumferential compressive stress, provide maximal radial tethering forces at the site of anastomosis, and actually dilate the vessel at the very location platelet aggregation occurs in the early post-operative phase. These important factors explain the increased success rate in the difficult model of the 0.4 mm. size inferior epigastric artery of the rat. With any constant level of surgical skill, the success rate of microvascular repair falls as the vessel size decreases. Of course, the degree of skill acquired by the surgeon is an important factor in the success rate of microvascular repair, and the use of the external ring technique may actually improve any given level of surgical skill.

The external ring provided by the application is simply formed and easy to use. In surgery, where several anastomoses need be performed, the external ring technique will substantially reduce the time of the operation. The multidirectional tethering helps to assure dilation of the passageway at the interconnection, and interconnection with a large blood passageway is generally assured. The technique draws the intima of the severed ends in tight apposition to each other providing a fluid-tight interconnection and exposure of blood substantially entirely with the intima reducing the chance of significant post operative thrombosis.

While the invention has been described in terms of a preferred embodiment, modifications obvious to one with ordinary skill in the art may be made without departing from the scope of the invention. The embodiment of the external ring, described herein, is simple; however, modifications in ring design will be made depending upon the material used and surgical considerations. Although the invention has been described in terms of a fully encircling member or ring, an incomplete, but substantially encircling ring member might be used instead allowing it to be slipped around the blood vessel after sutures have interconnected the blood vessel ends, and the tethering forces in the several radial directions could be relied upon to hold such an incomplete ring in place around the blood vessel.

Various features of the invention are set forth in the following claims.

What is claimed is:

1. A method of anastomosing a prepared living vessel end portion to a second prepared living vessel portion comprising
    substantially encircling the prepared living vessel end portion with a biocompatible member,
    connecting the prepared living vessel end portion to the second prepared living vessel portion with three or more sutures at circumferally spaced apart locations, and
    tethering said sutures to said member and stretching radially outward the living vessel portions at said connected portions in three or more different directions toward the biocompatible member to enlarge the vessel end portions, with the enlarged vessel portions trying to contract and forcing the intima of the vessel portions into sealing apposition.

2. A method according to claim 1 wherein a member is used which fully encircles the living vessel end portion and including the step of centering the encircling member over the juncture of the vessel portions prior to the tethering.

3. A method according to claim 1 using a member in the form of a ring, having an interior surface significantly larger than the outside surface of the living vessel end portion, said tethering tenting the connected vessel portions at the suture locations to provide an enlarged polygonal opening within the vessel end portion.

4. A method according to claim 1 using a member having preformed means for tethering said sutures thereto and including the step of drawing the living vessel portions at the connected locations radially outward into contact with a facing side of the encircling member.

5. A method of anastomosing a prepared living vessel end portion to a second prepared living vessel portion within a living body comprising
    substantially encircling the prepared living vessel end portion with a single biocompatible member having means for connecting vessel tissue thereto at three or more circumferally spaced-apart locations that are significantly radially outward of the exterior surface of said vessel end portion,
    tethering both of said vessel portions to said connecting means, stretching said vessel portions radially outward in three or more different directions and bringing the intima of the vessel portions into engagement with contraction forces from the expanded vessel portions urging the intima into sealing apposition, and
    leaving said member in the body to maintain patency of said tethered vessel portions along the anastomosis site as said blood vessel portions heal.

6. Apparatus for anastomosing a first living vessel of an external diameter having a prepared end and an open first passageway therein to a second living vessel having a second passageway and a prepared opening comprising a substantially encircling anastomosis member of biocompatible material having an internal wall with at least three locations spaced from the axial center of said member a distance at least about 50% greater than the external radius of said first vessel prepared end and at least three stretching connecting means spaced circumferentially about said anastomosis member and connected thereto for joining the end of the first vessel and the second vessel to said encircling member at said locations with the end of the first living vessel stretched radially outward to tent the same to enlarge the passageway therein and to assist in holding the end of the first vessel in sealing apposition against the second vessel, said encircling member being sufficiently rigid to maintain its shape while serving as the sole support of the joined vessels connected thereto.

7. An apparatus according to claim 6 with said substantially encircling member having no more than four connecting means.

8. An apparatus according to claim 6 wherein said connecting means include at least three sutures tethering said vessels to said member.

9. An apparatus according to claim 8 wherein said connecting means also include attachment means at said locations for positioning said sutures at said locations.

10. An apparatus according to claim 9 wherein said encircling member has an outer wall and a pair of radially extending sidewalls between said internal wall and said outer wall, and said attachments means are indentations in said sidewalls at said locations that reduce the axial dimension of said member at said locations.

11. An apparatus according to claim 10 wherein said attachment means are indentation pairs in said sidewalls at said locations.

12. An apparatus according to claim 6 with said substantially encircling member formed of material that is dissolved or degraded within a living body.

13. An apparatus according to claim 6 with said substantially encircling member having an annular configuration.

14. Apparatus for anastomosing a first living vessel of an external diameter having a prepared end and an open first passageway therein to a second living vessel having a second passageway and a prepared opening comprising a substantially encircling anastomosis member of biocompatible material having an internal wall with three or four connecting locations spaced from the axial center of said member a distance substantially greater than the external radius of said first vessel prepared end and a like number of stretching and connecting means for joining the end of the first vessel and the second vessel to said encircling member at said locations with the end of the first living vessel stretched radially outward to tent the same to enlarge the passageway therein and to assist in holding the end of the first vessel in sealing apposition against the second vessel, said encircling member being sufficiently rigid to maintain its shape while serving as the sole support of said joined vessels connected thereto.

15. An apparatus according to claim 14 with said substantially encircling anastomosis member having three connecting means at three locations.

16. An apparatus according to claim 14 wherein said connecting means includes three or four sutures tethering said vessels to said member.

17. An apparatus according to claim 16 wherein said connecting means includes attachment means at said locations for positioning said sutures at said locations.

18. An apparatus according to claim 17 wherein said encircling member has an outer wall and a pair of radially extending sidewalls between said internal wall and said outer wall, and said attachments means are indentations in the sidewalls at said locations that reduce the axial dimension of the member at said locations.

19. An apparatus according to claim 18 wherein said attachment means are indentation pairs in the sidewalls at said locations.

20. An apparatus according to claim 14 with said substantially encircling member formed of material that is dissolved or degraded within a living body.

21. An apparatus according to claim 14 with said substantially encircling member having an annular configuration.

* * * * *

UNITED STATES PATENT AND TRADEMARK OFFICE
CERTIFICATE OF CORRECTION

PATENT NO. : 4,474,181

DATED : October 2, 1984

INVENTOR(S) : Robert R. Schenck

It is certified that error appears in the above-identified patent and that said Letters Patent is hereby corrected as shown below:

On the title page;

After "Schenck" in the heading, insert --et al.--.

After "[76]", change "inventor" to --inventors--.

After "Ill. 60611" insert --and Harry P. Weinrib, 2644 West Estes Avenue, Chicago, Illinois 60645--.

Signed and Sealed this

Thirtieth Day of July 1985

[SEAL]

Attest:

DONALD J. QUIGG

Attesting Officer     Acting Commissioner of Patents and Trademarks